United States Patent [19]

Wu

[11] Patent Number: 5,221,774
[45] Date of Patent: Jun. 22, 1993

[54] ETHYLENE OLIGOMERIZATION

[75] Inventor: An-hsiang Wu, Bartlesville, Okla.

[73] Assignee: Phillips Petroleum Company, Bartlesville, Okla.

[21] Appl. No.: 854,042

[22] Filed: Mar. 19, 1992

[51] Int. Cl.$^5$ .............................................. C07C 2/08
[52] U.S. Cl. .................................... 585/520; 585/523; 585/527; 585/530; 585/531; 502/325
[58] Field of Search .............. 585/514, 511, 521, 510, 585/523, 531, 520, 530

[56] References Cited

U.S. PATENT DOCUMENTS

| | | | |
|---|---|---|---|
| 3,390,195 | 6/1968 | Chappel et al. | 260/666 |
| 4,020,121 | 4/1977 | Kister et al. | 260/683.15 |
| 4,482,640 | 11/1984 | Knudsen et al. | 502/155 |
| 4,518,814 | 5/1985 | Knudsen et al. | 585/323 |
| 4,716,138 | 12/1987 | Murray | 502/117 |

*Primary Examiner*—Asok Pal
*Assistant Examiner*—P. Achutamurthy
*Attorney, Agent, or Firm*—William R. Sharp

[57] ABSTRACT

An ethylene oligomerization process is provided wherein ethylene is contacted with a nickel(II) halide compound, a phosphine compound and a zinc component in a solvent to produce a precursor reaction mixture, followed by contacting ethylene with the precursor reaction mixture and a fluorinated organoacid to produce a product reaction mixture comprising the desired oligomerization product.

18 Claims, No Drawings

ETHYLENE OLIGOMERIZATION

This invention relates to a process for oligomerizing ethylene to an oligomerization product. The term "oligomerization product" as used herein and in the appended claims is defined as including olefinic oligomers of ethylene, i.e. $C_nH_{2n}$ where n=4, 6, 8, 10, . . . The simpler notation of $C_n$ will be used hereafter to denote such oligomers.

Olefins, including α-olefins or 1-olefins, have become very important products in the chemical industry. Through hydroformylation, copolymerization and arylation/sulfonation, the 1-olefins become components of plasticizers, solvents, plastics, surfactants, synthetic lubricants, fatty acids and detergents. Production of 1-olefins by oligomerizing ethylene has been previously investigated to a considerable extent, such as in processes employing nickel catalyzed oligomerization, but further development would be desirable in regard to achieving a desirable combination of productivity, selectivity to 1-olefins and distribution (primarily $C_4$'s-$C_{10}$'s) of oligomers in the oligomerization product.

It is, therefore, an object of the invention to provide a process for oligomerizing ethylene which achieves the above-mentioned desired combination of results.

The above object is achieved by a process for oligomerizing ethylene to an oligomerization product comprising the steps of: (a) contacting ethylene, a nickel(II) halide compound, a phosphine compound of the formula $PR_3$ where R independently represents H or a $C_1$ to $C_{20}$ hydrocarbyl radical and where at least one R is not H, and a zinc component selected from the group consisting of elemental zinc and an organozinc compound, wherein the ethylene is in a gaseous phase and the nickel(II) halide, phosphine compound and zinc component are in a solvent and in a liquid phase, thereby producing a precursor reaction mixture in a liquid phase; and (b) contacting, after step (a), ethylene in a gaseous phase, the precursor reaction mixture, and a fluorinated organoacid in a liquid phase, thereby producing a product reaction mixture in a liquid phase comprising the oligomerization product. The fluorinated organoacid in step (b) can optionally also be in a solvent, which can be the same as or different than the solvent used in step (a).

As used herein and in the appended claims, the term "nickel(II) halide compound" is defined as having a molecular structure with a nickel atom at a valence state of +2 and at least two ligands which are halogen (Cl, Br, I or F) atoms. Nickel(II) chloride compounds are preferred. The nickel(II) halide can have only the two halogen ligands ("anhydrous"), but can also be in a form which has additional ligands such as $H_2O$ or organic ligands complexed with the nickel atom. Examples of such nickel(II) halide compounds are nickel(II) chloride hexahydrate and nickel(II) chloride dimethoxyethane, of which nickel(II) chloride dimethoxyethane generally optimizes productivity and selectivity to 1-olefins.

Suitable phosphine compounds of the formula $PR_3$, where R independently represents H or a $C_1$ to $C_{20}$ hydrocarbyl radical and where at least one R is not H, include cyclohexylphosphine, dicyclohexylphosphine, tricyclohexylphosphine, tri-n-hexylphosphine, triethylphosphine, triisopropylphosphine, triisobutylphosphine, tri-n-butylphosphine, tri-t-butylphosphine, phenylphosphine, diphenylphosphine, triphenylphosphine, diphenylcyclohexylphosphine, diethylphenylphosphine, ortho-tolyldiphenylphosphine, di(ortho-tolyl)phenylphosphine and tribenzylphosphine. Tricyclohexylphosphine is generally preferred as optimizing productivity and as giving the optimum distribution of oligomers in the $C_4$-$C_{10}$ range.

As noted above, the zinc component is selected from the group consisting of elemental zinc (in the form of, for example, zinc "dust") and an organozinc compound. The organozinc compound is preferably of the formula $R_2'Zn$ where R' is a $C_1$ to $C_{12}$ hydrocarbyl radical. Suitable organozinc compounds of the formula $R_2Zn$ include dimethylzinc, diethylzinc, di-n-propylzinc, di-n-butylzinc, diphenylzinc and di-o-tolylzinc. Those organozinc compounds where R' is a $C_1$ to $C_{12}$ (preferably $C_1$ to $C_6$) alkyl radical are generally preferred, of which diethylzinc is most preferred. As shown in subsequent examples, an organozinc compound such as diethylzinc generally optimizes productivity as compared to zinc dust when used in conjunction with nickel(II) chloride dimethoxyethane.

The preferred fluorinated organoacid is a fluorinated carboxylic acid of the formula $R''COOH$ where $R''$ represents a $C_1$ to $C_{10}$ fluorinated hydrocarbyl radical having at least one fluorine (F) atom. Suitable fluorinated carboxylic acids include trifluoroacetic acid, heptafluorobutyric acid, difluoroacetic acid, pentafluoropropionic acid and perfluoroadipic acid. The preferred fluorinated carboxylic acid is trifluoroacetic acid. Fluorinated organoacids also within the scope of certain broad aspects of the invention are fluorinated sulfonic acids such as trifluoromethanesulfonic acid and heptafluoroethanesulfonic acid.

The preferred molar ratio of (i) the phosphine compound, (ii) the zinc component, and (iii) the fluorinated organoacid, respectively, to the nickel(II) halide compound are as follows: (i) about 0.1-5 to 1, most preferably about 0.8-1.2 to 1; (ii) about 1-10 to 1, most preferably about 1.5-2.5 to 1; and (iii) about 1-20 to 1, most preferably about 5-7 to 1.

As noted previously, the nickel(II) halide compound, phosphine compound and zinc component are in a solvent in step (a), and the fluorinated organoacid is optionally in a solvent in (b). Such solvent can be selected from the group consisting of: at least one saturated hydrocarbon or fluorinated hydrocarbon of the formula $C_nH_{2n+2-x}F_x$ where n=4, 5, 6, 7 or 8 and x=0, 1 or 2; at least one aromatic hydrocarbon or fluorinated hydrocarbon of the formula $C_6H_{6-n}(R''')_n$ where n=0, 1, 2, 3, or 4 and $R'''$ independently represents F or a $C_1$ to $C_6$ alkyl radical or fluorinated alkyl radical; and mixtures thereof. Suitable saturated hydrocarbons or fluorinated hydrocarbons include isobutane, isopentane, neohexane, n-heptane, n-pentane, n-hexane, octane, isooctane, perfluroalkanes and fluorinated alkanes. Suitable aromatic hydrocarbons or fluorinated hydrocarbons include toluene, benzene, ethylbenzene, xylene (o,p,m), α,α,α-triflurotoluene, 2-fluorotoluene, 3-fluorotoluene, 4-fluorotoluene, fluorobenzene, difluorobenzene (1,2; 1,3; 1,4) and difluorotoluene (2,4; 2,5; 2,6; 3,4). Aromatic hydrocarbons are generally preferred.

The weight ratio of the total amount of solvent employed in the process to the combination of the nickel(II) halide compound, phosphine compound, zinc component and fluorinated organoacid can be in the broad range of about 1-$10^6$ to 1, most preferably in the range of about 5-10,000 to 1. The amount of solvent employed depends upon the cost, ease of oligomerization product recovery therefrom, reactor size, and other practical considerations.

The particular procedure by which the various reagents are contacted as in (a) and (b) above can take a variety of forms.

In accordance with step (a), the nickel(II) halide compound, phosphine compound, and zinc component in the solvent and in liquid phase can be contacted with ethylene in gaseous phase in a first vessel by agitating the liquid phase therein and pressuring the first vessel with the ethylene to a predetermined pressure.

In accordance with step (b), the acid (optionally in a solvent) can be added to a second vessel, and either the precursor reaction mixture resulting from step (a) can be transferred from the first vessel to the second vessel or the acid can be transferred to the first vessel. In either case, the precursor reaction mixture and acid are preferably agitated in whichever vessel receives all liquid reagents and such vessel is pressured with ethylene to a predetermined reaction pressure. Most preferably, the acid is contacted with ethylene in the second vessel prior to contacting with the precursor reaction mixture.

The vessel in which step (b) is carried out can be an autoclave or other similar pressure reactor, and the vessel in which step (a) is carried out can be such a reactor or an associated addition vessel, depending on the particular procedure employed.

Pressure and temperature conditions in steps (a) and (b) are such that the ethylene is in a gaseous phase and the nickel(II) halide compound, phosphine compound and zinc component as in a solvent and the acid as optionally in a solvent are in the liquid phase. Preferably, step (a) is carried out at a pressure of about 5 to 5000 psig and a temperature of about $-100°$ C. to about $100°$ C., most preferably at a pressure of about 20 to about 1000 psig and a temperature of about $50°$ C. to about $75°$ C. Step (b) is preferably carried out at a pressure of about 5 to about 5000 psig and a temperature of about $0°$ C. to about $125°$ C., most preferably at a pressure of about 200 to about 1000 psig and a temperature of about $20°$ C. to about $50°$ C.

With respect to time, step (a) is preferably carried out for a time of about 1 minute to about 6 hours, most preferably about 15 minutes to about 3 hours. Step (b) is preferably carried out for a time of about 1 minute to about 15 hours, most preferably about 15 minutes to about 5 hours.

The oligomerization product as contained in the product reaction mixture resulting from step (b) can be separated and recovered from the product reaction mixture by conventional means such as fractional distillation. As demonstrated in examples to follow, the oligomerization product contains a desirable distribution of primarily $C_4$-$C_{10}$ oligomers.

Many variations of the invention are possible in the light of the above teachings. For example, although the invention is described above in terms of a batchwise process, it is within the scope of certain broad aspects of the invention to employ a continuous process wherein ethylene is passed continuously into a reaction zone while product reaction mixture containing the oligomerization product is concomitantly withdrawn therefrom.

Examples are set forth below which further illustrate the invention but which should not be construed to limit the invention in any manner.

Each example employed a 300 mL stainless steel (316SS) Autoclave Engineers stirred tank autoclave, hereafter denoted simply as a reactor. Other equipment employed in individual examples will be referenced in those examples. It is understood that the contents of such a reactor in the following examples are being agitated, typically at a slow agitation of about 300 rpm during purging of the reactor or addition of various reagents to the reactor, and at a normal agitation of about 1600 rpm at all other times.

Product analysis was performed on approximately 5 gram samples with an HP 5890 II GC-FID Spectrometer equipped with a capillary DB-1 (60 m) column. The column was operated at $30°$ C. for 5 minutes, followed by a $15°$ C./minute increase to $285°$ C. which was held for 13 minutes. Detection was obtained using a flame ionization detector in the area percent mode. Selectively and weight percent distribution, discussed further below, were determined from spectra as recorded by the spectrometer.

In the following examples, results are reported in terms of productivity, selectivity to 1-olefins and weight percent distribution of oligomerization product. Productivity is defined as the grams of oligomerization product produced per gram of Ni per hour, and was calculated in each example based on grams of ethylene reacted. Selectivity to 1-olefins is given in terms of the weight percent of various fractions ($C_n$, $n=4,6,8,...$) of the oligomerization product which is 1-olefin. The distribution of the oligomerization product is given as the weight percent of the various fractions of the total oligomerization product.

EXAMPLE I

This example demonstrates ethylene oligomerization employing nickel(II) chloride hexahydrate, zinc dust, a variety of phosphine compounds and trifluoroacetic acid in different solvents. This example further demonstrates the composition of the precursor reaction mixture before addition of the acid, and the lack of oligomers in such precursor reaction mixture.

A reactor was purged with nitrogen for about 5 minutes followed by addition of 48 mL of a solvent indicated in Table I, zinc dust (0.131 g; 2.0 mmol), a phosphine compound (1.0 mmol) indicated in Table I and the nickel(II) chloride hexahydrate (0.238 g; 1.00 mmol). The reactor was then sealed, purged with ethylene several times (4–6), and then pressured to 200 psig with ethylene and heated to $60°$ C. via the application of an external heating mantle. This pressure and temperature was maintained for 60 minutes.

Trifluoroacetic acid (0.570 g; 5.00 mmol) and 2 mL of the solvent indicated in Table I were added to a 40 mL addition vessel by the use of a syringe. The vessel was immediately sealed and pressured with ethylene to 700 psig. The contents of the addition vessel, including the ethylene, were then transferred to the reactor through its addition valve at the end of the above-mentioned 60 minute period. The internal reaction pressure was maintained at 700 psig and the reactor temperature maintained at $40°$ C. by means of either external cooling water or heating for the reaction period (Rx time in minutes) indicated in Table I.

At the end of the reaction period, a sample of the product reaction mixture was taken from the reactor through its sample valve into a 50 mL pressure sample tube, and was analyzed as described above. The resulting selectivity and weight distribution data, along with corresponding phosphine compound, solvent and productivity, are set forth in Table I. It is understood that runs 2-5, 7-8, and 10-11 use the same phosphine compound as runs 1, 6 and 9, respectively. A similar notation is used in subsequent examples.

The runs of this example were carried out as described in Example I except that diethylzinc was employed instead of zinc dust by adding 2.0 mL of a 1.1M

TABLE I

| Run | Phosphine | Solvent | Rx Time | Productivity | Distribution wt. % of $C_n$ (n = 4,6,8,10,12,14 and higher) | Selectivity wt. % of 1-$C_n$ (n = 4,6,8,10) |
|---|---|---|---|---|---|---|
| 1 | Tricyclohexylphosphine | Benzene | 180 | 105 | 38,29,18,10,4,1 | 72,70,69,68 |
| 2 | | Toluene | 180 | 238 | 34,28,20,11,5,2 | 82,82,80,79 |
| 3 | | p-xylene | 180 | 206 | 31,29,21,12,5,2 | 85,85,84,83 |
| 4 | | Fluorobenzene | 180 | 227 | 32,28,20,11,6,3 | 81,81,80,78 |
| 5 | | n-heptane | 240 | 82 | 68,22,8,2,0,0, | 77,75,74,73 |
| 6 | Dicyclohexylphosphine | Benzene | 240 | 122 | 48,28,13,7,3,1 | 73,72,70,69 |
| 7 | | Toluene | 180 | 163 | 42,25,16,9,5,3 | 83,82,82,81 |
| 8 | | p-xylene | 180 | 178 | 36,27,18,10,6,3 | 82,82,81,80 |
| 9 | Cyclohexylphosphine | Benzene | 180 | 96 | 61,25,8,4,2,0 | 75,73,73,72 |
| 10 | | Toluene | 180 | 142 | 57,28,11,3,1,0 | 88,85,84,84 |
| 11 | | p-xylene | 180 | 175 | 55,27,12,4,2,0 | 84,84,83,83 |
| 12 | Tri-n-butylphosphine | Toluene | 180 | 65 | 76,19,4,1,0,0 | 67,65,66,65 |
| 13 | Triphenylphosphine | Toluene | 180 | 147 | 73,19,6,2,0,0 | 75,73,72,71 |
| 14 | Diphenylphosphine | Toluene | 180 | 124 | 80,16,3,1,0,0 | 82,82,80,79 |

The results shown in Table I indicate that the distribution of the oligomerization product varies among the different phosphine compounds and solvents, but in each run is mostly lower than $C_{12}$ olefins. Productivities range from 65 to over 200 g/g/hr, again depending upon the particular phosphine compound and solvent which is used. Selectivity to 1-olefins ranges from less than 70 weight percent to nearly 90 weight percent.

To determine the composition of the precursor reaction mixture before addition of the trifluoroacetic acid and whether or not any oligomerization occurs before addition of such acid, a sample of the precursor reaction mixture was taken from the reactor at the end of the above described 60 minute period in run 2. Such sample was analyzed as described previously. The analysis revealed no oligomers in the precursor reaction mixture.

EXAMPLE II

This example demonstrates ethylene oligomerization employing nickll(II) chloride hexahydrate, diethylzinc, a variety of phosphine compounds and trifluoroacetic acid in different solvents.

solution of diethylzinc (2.20 mmol) in toluene to the reactor by means of a syringe after addition of the solvent, nickel chloride hexahydrate and phosphine compound. Each run of this example had a reaction period of 3 hours. Results are shown in Table II.

TABLE II

| Run | Phosphine | Solvent | Productivity | Distribution wt. % of $C_n$ (n = 4,6,8,10,12,14 and higher) | Selectivity wt. % of 1-$C_n$ (n = 4,6,8,10) |
|---|---|---|---|---|---|
| 15 | Tricyclohexylphosphine | Benzene | 110 | 36,27,19,11,5,2 | 70,68,67,66 |
| 16 | | Toluene | 222 | 33,28,21,11,5,2 | 81,81,80,78 |
| 17 | | p-xylene | 235 | 32,28,21,12,5,2 | 84,83,83,81 |
| 18 | | Flurobenzene | 206 | 34,29,19,10,5,3 | 81,80,80,79 |
| 19 | | n-heptane | 91 | 65,27,6,2,0,0 | 75,75,74,74 |
| 20 | Dicyclohexylphosphine | Benzene | 175 | 46,29,14,7,3,1 | 72,71,70,70 |
| 21 | | Toluene | 138 | 40,31,17,8,3,1 | 85,84,84,83 |
| 22 | | p-xylene | 194 | 41,28,18,9,3,1 | 86,85,83,82 |
| 23 | Cyclohexylphosphine | Benzene | 78 | 68,24,6,2,0,0 | 84,83,82,81 |
| 24 | | Toluene | 102 | 59,27,9,4,1,0 | 84,84,84,82 |
| 25 | | p-xylene | 157 | 64,24,8,3,1,0 | 84,84,83,83 |

The results of Table II are similar to those shown in Table I, indicating that an organozinc compound such as diethylzinc is also effective as a zinc component in ethylene oligomerization in accordance with the invention.

EXAMPLE III

This example demonstrates ethylene oligomerization employing nickel(II) chloride dimethoxyethane, zinc dust, a number of phosphine compounds and trifluroacetic acid in toluene solvent.

The runs of this example were carried out as described in Example I except for the following: nickel(II) chloride dimethoxyethane (0.220 g; 1.00 mmol) was used instead of nickel(II) chloride hexahydrate; different reaction temperatures (Rx Temp. in °C.) were employed in the various runs as indicated in Table III; and toluene was used as the solvent in each run. Results are shown in Table III.

TABLE III

| Run | Phosphine | Rx Temp. | Rx Time | Productivity | Distribution wt. % of $C_n$ (n = 4,6,8,10,12,14 and higher) | Selectivity wt. % of 1-$C_n$ (n = 4,6,8,10) |
|---|---|---|---|---|---|---|
| 26 | Triphenylphosphine | 33 | 240 | 148 | 91,9,0,0,0,0 | 90,86,n/a,n/a |
| 27 | Tricyclohexylphosphine | 37 | 180 | 428 | 28,29,21,13,6,3 | 90,90,82,80 |

TABLE III-continued

| Run | Phosphine | Rx Temp. | Rx Time | Productivity | Distribution wt. % of $C_n$ (n = 4,6,8,10,12,14 and higher) | Selectivity wt. % of 1-$C_n$ (n = 4,6,8,10) |
| --- | --- | --- | --- | --- | --- | --- |
| 28 | Tri-n-hexylphosphine | 36 | 240 | 335 | 84,16,0,0,0,0 | 91,90,n/a,n/a |
| 29 | Tri-n-butylphosphine | 34 | 240 | 284 | 82,18,0,0,0,0 | 92,87,n/a,n/a |

The results of Table III show that nickel(II) chloride dimethoxyethane is also an effective nickel(II) chloride compound in ethylene oligomerization in accordance with the invention. Moreover, run 27 had about the same reaction conditions and also used the same reagents and solvent as run 2 of Example I, except for the nickel(II) chloride compound, thus making these runs directly comparable. It can be seen from Tables I and III that nickel chloride(II) dimethoxyethane as employed in run 27 resulted in a higher productivity and higher selectivity to 1-olefins than nickel(II) chloride hexahydrate as employed in run 2.

EXAMPLE IV

This example demonstrates ethylene oligomerization employing nickel(II) chloride dimethoxyethane, diethyl zinc, a phosphine compound and trifluoroacetic acid in toluene solvent.

The runs of this example were carried out as in Example III, except that diethylzinc was employed instead of zinc dust by adding 2.0 mL of a 1.1M solution of diethylzinc (2.20 mmol) in toluene to the reactor by means of a syringe after addition of the solvent, nickel(II) chloride dimethoxyethane and phosphine compound. Results are shown in Table IV.

TABLE IV

| Run | Phosphine | Rx Temp. | Rx Time | Productivity | Distribution wt. % of $C_n$ (n = 4,6,8,10,12,14 and higher) | Selectivity wt. % of 1-$C_n$ (n = 4,6,8,10) |
| --- | --- | --- | --- | --- | --- | --- |
| 30 | Triphenylphosphine | 30 | 240 | 205 | 95,5,0,0,0,0 | 89,84,n/a,n/a |
| 31 | Tricyclohexylphosphine | 35 | 180 | 634 | 30,29,20,12,6,3 | 90,88,81,78 |
| 32 | Tri-n-hexylphosphine | 37 | 180 | 410 | 84,14,0,0,0,0 | 91,89,n/a,n/a |
| 33 | Tri-n-butylphosphine | 34 | 240 | 265 | 87,13,0,0,0,0 | 90,85,n/a,n/a |

A comparison of runs 30-33 of this example with runs 26-29 of Example III indicates generally higher productivities with nickel(II) chloride dimethoxyethane/diethylzinc as compared to nickel(II) chloride dimethoxyethane/zinc dust, except in run 33 with tri-n-butylphosphine which gave results similar to those results in run 29.

That which is claimed is:

1. A process for oligomerizing ethylene to an oligomerization product comprising:
   (a) contacting ethylene, nickel(II) chloride hexahydrate, a phosphine compound of the formula $PR_3$ where R independently represents H or a $C_1$ to $C_{20}$ hydrocarbyl radical and where at least one R is not H, and a zinc component selected from the group consisting of elemental zinc and an organozinc compound, wherein the ethylene is in a gaseous phase and the nickel(II) chloride hexahydrate, phosphine compound, and zinc component are in a solvent and in a liquid phase, thereby producing a precursor reaction mixture in a liquid phase;
   (b) contacting, after step (a), ethylene in a gaseous phase, the precursor reaction mixture, and trifluoroacetic acid in a liquid phase, thereby producing a product reaction mixture in a liquid phase comprising the oligomerization product.

2. A process as recited in claim 1 wherein step (a) is carried out at a pressure of about 5 to about 5000 psig, at a temperature of about $-100°$ C. to about $100°$ C., and for a time of about 1 minute to about 6 hours.

3. A process as recited in claim 2 wherein step (a) is carried out at a pressure of about 20 to about 1000 psig, at a temperature of about $50°$ C. to about $75°$ C., and for a time of about 15 minutes to about 3 hours.

4. A process as recited in claim 1 wherein step (b) is carried out at a pressure of about 5 to about 5000 psig, at a temperature of about $0°$ C. to about $125°$ C., and for a time of about 1 minute to about 15 hours.

5. A process as recited in claim 4 wherein step (b) is carried out at a pressure of about 200 to about 1000 psig, at a temperature of about $20°$ C. to about $50°$ C., and for a time of about 15 minutes to about 5 hours.

6. A process recited in claim 1 wherein the trifluoroacetic acid is contacted with ethylene prior to step (b).

7. A process as recited in claim 1 wherein the organozinc compound is of the formula $R_2'Zn$ where $R'$ is a $C_1$ to $C_{12}$ hydrocarbyl radical.

8. A process as recited in claim 7 wherein $R'$ is a $C_1$ to $C_{12}$ alkyl radical.

9. A process as recited in claim 8 wherein the zinc component is diethylzinc.

10. A process as recited in claim 1 wherein the molar ratio of (i) the phosphine compound, (ii) the zinc component, and (iii) trifluoroacetic acid, respectively, to the nickel(II) chloride hexahydrate are as follows: (i) about 0.1-5 to 1; (ii) about 1-10 to 1; and (iii) about 1-20 to 1.

11. A process as recited in claim 1 wherein the solvent is selected from the group consisting of: at least one saturated hydrocarbon or fluorinated hydrocarbon of the formula $C_nH_{2n+2-x}F_x$ where n=4, 5, 6, 7 or 8 and x=0, 1 or 2; and at least one aromatic hydrocarbon or fluorinated hydrocarbon of the formula $C_6H_{6-n}(R''')_n$ where n=0, 1, 2, 3 or 4 and $R'''$ independently represents F or a $C_1$ to $C_6$ alkyl radical or fluorinated alkyl radical; and mixtures thereof.

12. A process as recited in claim 11 wherein the solvent is said aromatic hydrocarbon.

13. A process as recited in claim 11 wherein the trifluoroacetic acid in (b) is also in a solvent selected from the group consisting of said saturated hydrocarbon or fluorinated hydrocarbon and said aromatic hydrocarbon or fluorinated hydrocarbon.

14. A process for oligomerizing ethylene to an oligomerization product comprising:
(a) contacting ethylene, nickel(II) chloride dimethoxyethane, tricyclohexylphosphine, and a zinc component selected from the group consisting of elemental zinc and an organozinc compound, wherein the ethylene is in a gaseous phase and the nickel(II) chloride dimethoxyethane, tricyclohexylphosphine, and zinc component are in a solvent and in a liquid phase, thereby producing a precursor reaction mixture in a liquid phase; and
(b) contacting, after step (a), ethylene in a gaseous phase, the precursor reaction mixture, and trifluoroacetic acid in a liquid phase, thereby producing a product reaction mixture in a liquid phase comprising the oligomerization product.

15. A process as recited in claim 14 wherein the zinc component is an organozinc compound.

16. A process as recited in claim 15 wherein the zinc component is diethylzinc.

17. A process as recited in claim 1 wherein the zinc component is elemental zinc.

18. A process as recited in claim 14 wherein the zinc component is elemental zinc.

* * * * *